United States Patent [19]
Lemonnier

[11] Patent Number: 5,288,638
[45] Date of Patent: Feb. 22, 1994

[54] APPARATUS AND METHOD FOR THE MICROBIOLOGICAL TESTING OF PRESSURIZED LIQUIDS

[75] Inventor: Jean Lemonnier, le Vesinet, France

[73] Assignee: Millipore Corporation, Bedford, Mass.

[21] Appl. No.: 895,291

[22] Filed: Jun. 8, 1992

[30] Foreign Application Priority Data

Jun. 13, 1991 [FR] France ............... 9107232

[51] Int. Cl.⁵ ............... B01D 29/00; C12M 1/12
[52] U.S. Cl. ............... 435/299; 435/292; 435/297; 435/298; 435/311; 422/101; 210/244; 210/476; 210/477
[58] Field of Search ............... 435/30, 34, 284, 285, 435/287, 291, 292, 294, 296, 299, 311; 422/101; 210/464, 476, 477, 244; 220/367, 368, 371, 372

[56] References Cited
U.S. PATENT DOCUMENTS

| | | | |
|---|---|---|---|
| 2,879,207 | 3/1959 | Poitras | 435/311 |
| 2,904,857 | 9/1959 | Goetz | 435/30 |
| 3,448,011 | 6/1969 | Russomanno | 435/287 |
| 4,777,137 | 10/1988 | Lemonnier | 435/299 |
| 5,202,262 | 4/1993 | Lemonnier | 435/311 |

Primary Examiner—Robert J. Warden
Assistant Examiner—T. A. Trembley
Attorney, Agent, or Firm—Andrew T. Karnakis; Paul J. Cook

[57] ABSTRACT

An apparatus for the microbiological testing of pressurized liquids is disclosed which includes a completely closed container, at the base of which a membrane filter is sealed. Fitted upstream from the membrane is a built-in reading window and included downstream from the membrane, is a flange comprising a lip seal and a female threaded part. The apparatus may be used in conjunction with a microbiological testing process by screwing to the container a filtration support, taking and filtering the sample to be analyzed, and then substituting for the support an incubation cartridge for the subsequent development, in an incubator, of the colonies collected on the membrane.

12 Claims, 10 Drawing Sheets

APPARATUS AND METHOD FOR THE MICROBIOLOGICAL TESTING OF PRESSURIZED LIQUIDS

FIELD OF THE INVENTION

This invention concerns an apparatus and method for the microbiological testing of pressurized liquids, which serves to count the living microorganisms contained in these liquids.

BACKGROUND OF THE INVENTION

In many industries, including the food, pharmaceutical and electronics industries, it is important to be able to check the microbiological quality of pressurized fluids, whether during transfer of such fluids through lines or whether such fluids are kept in storage tanks.

So far, the standard method used has been to sample, in aseptic conditions, a certain volume of liquid in a receptacle with the aid of a small sample valve and then to test this sample by the usual filtration method or the method described in U.S. Pat. No. 4,777,137 filed on Jan. 15, 1985 and assigned to Millipore Corporation.

It is easy to imagine the risks of "false positives" incurred by these samples and various transfer of samples. Moreover, these different operations waste time and cause delays in receiving the results of the analyses. The invention described below eliminates these risks because the filtration necessary for the analysis, as well as the placing of the filter in contact with the nutrient medium, which is necessary for the development of the microorganisms that are retained on the membrane, can be carried out in the field. Accordingly, this feature simplifies the operations hitherto necessary for the microbiological testing of these liquids.

SUMMARY OF THE INVENTION

The apparatus for the microbiological testing of a liquid sample according to the present invention is a device, preferably pre-sterilized and adapted for single use only, which makes use of a membrane filter. This device is characterized by a completely closed container of transparent plastic, at the base of which a membrane filter is sealed, the container being fitted, upstream from the membrane, with a built-in reading window and, downstream from the membrane, with a flange having a lip seal and a female threaded part. A filtration support or an incubation cartridge, both made of plastic, can be fitted to the female threaded part of the container.

The filtration support has a chamber fitted externally with a male threaded part cooperating with the female threaded part of the container and an upper plate fitted with a system of drainage channels terminating in an axial outlet orifice. The filtration support also includes a sealing cone cooperating with the lip seal of the container to prevent any infiltration or contamination from the exterior on the periphery of the support during the filtration of the liquid sample to be analyzed.

The incubation cartridge comprises a chamber containing a suitable liquid or dry microorganism culture medium fitted externally with a male threaded part cooperating with the female threaded part of the container. The cartridge may also possibly contain at its upper end a conical part designed to cooperate with the lip seal of the container to guarantee the seal on the downstream periphery of the membrane filter and thus to prevent any dehydration of the culture medium during incubation.

The device according to the invention offers the advantage of maintaining the membrane filter in a perfectly closed container, hence sheltered from any exogenous contamination liable to distort the results of the micro biological analysis to be performed. The closed container configuration also serves to allow the liquid sample to be analyzed under pressures up to $6 \cdot 10^5$ Pa, which was not the case of any previously known device. In addition, the present device also serves to carry out the incubation of any microorganisms collected on the membrane filter directly and rapidly and without any handling of the membrane.

The present invention is also designed for a process of microbiological testing of a liquid sample using a membrane filter which comprises in succession the introduction of the sample to be analyzed in a device comprising the container defined above screwed to a filtration support, the positive or negative pressurization of the container to terminate the filtration, the replacement of the filtration support by an incubation cartridge screwed into the container, and incubation of the assembly consisting of the container and the cartridge in an incubator.

It should be noted that such a process, independent of its simplicity and its speed, serves to check the microbiological quality of a pressurized liquid with maximum reliability because it avoids any handling of the liquid sample or of the membrane which collects any microorganisms present which are to be detected.

BRIEF DESCRIPTION OF THE DRAWINGS

The invention will now be described with the aid of the enclosed drawings, where.

DETAILED DESCRIPTION OF THE INVENTION

Figure 1:
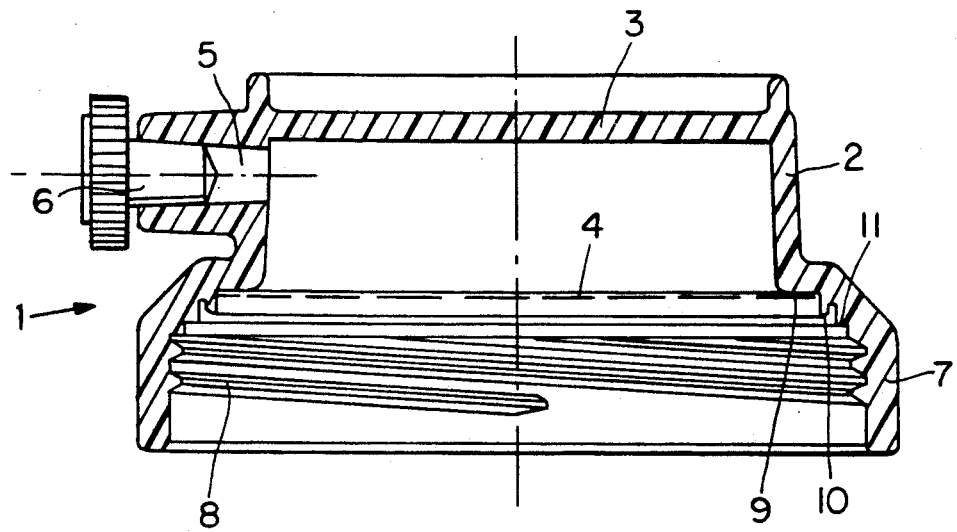
FIG. 1 shows an elevation section of the container of the device according to the invention.
Figure 2:
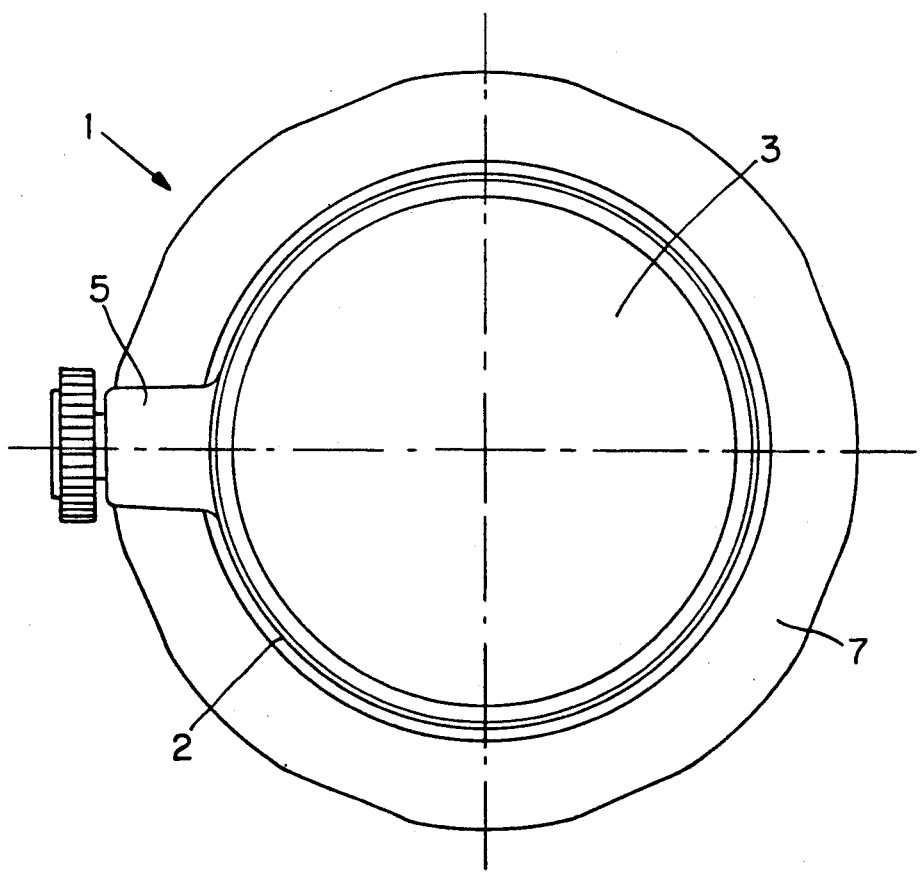
FIG. 2 is a plan view of the container shown in FIG. 1.

The reservoir 1, shown in FIGS. 1 and 2, comprises an integral, sealed body 2, of generally cylindrical shape, closed at its upper part by a reading window 3, and, at its lower part, by a membrane filter 4, located in a plane parallel to that of the reading window.

The cylindrical body 2 is fitted with a side inlet orifice 5 of the female Luer type, which can be closed by a male Luer plug 6 and whose axis is parallel to the plane of the membrane 4. A tubular flange 7, with a larger diameter than that of the cylindrical body 2, prolongs this body downstream from the membrane filter and is fitted internally with a female threaded part 8, which can consist in particular of three female thread initiations to guarantee rapid clamping to a removable element (not shown) fitted with corresponding male threads.

The connecting part between the cylindrical body 2 and the tubular flange 7 comprises in succession, from upstream to downstream, a shoulder 9, a lip seal 10 and a locking stop 11. The shoulder 9, in the form of a circular ring with the same axis as that of the body 2, delimits the base of the container 1 to which the membrane filter 4 is sealed in a plane perpendicular to the common axis of the body 2 and the flange 7.

The lip seal 10 in the embodiment shown in FIG. 1 is in the form of a circular tab with an intermediate diameter between that of the body 2 and of the flange 7, and with the same axis as the latter two, extending axially with the internal and external faces. The locking stop 11, also in the form of a circular ring with the same axis as the cylindrical body 2, is intended to prevent the crushing of the circular end of the membrane filter during the screwing of the removable element to the threaded part 8 of the flange.

As shown in FIG. 1, the reading window 3 is clear of any obstruction which would mask the view of the membrane filter 4. The container 1 is made of plastic that is transparent, pressure-resistant, and susceptible to perforation without fracture (preferably laterally) to permit, if needed, the sampling of a microbe colony that has developed after incubation on the membrane filter. A suitable plastic for the container is a copolymer of methyl methacrylate, butadiene and styrene.

The membrane filter can generally be formed of cellulose ester, with a pore diameter that varies according to the size of the microorganism to be retained. For commonly determined microorganisms, the pore diameter generally used is 0.45 $\mu$m. Other membrane filter materials, hydrophilic or hydrophobic, can be used for the retention of other microorganisms as is well appreciated by those of skill in the art.

Figure 3:
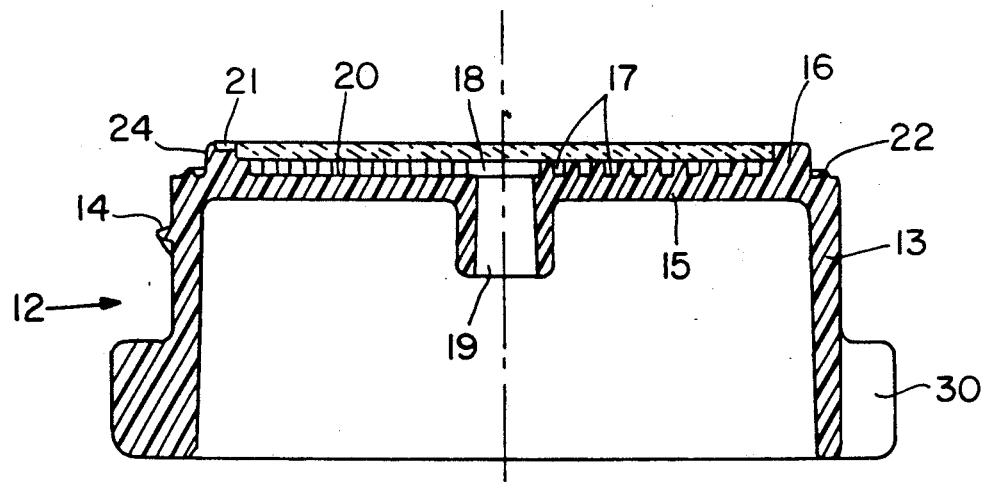
FIG. 3 is an elevation section of the filtration support designed to cooperate with the container of FIGS. 1 and 2.
Figure 4:
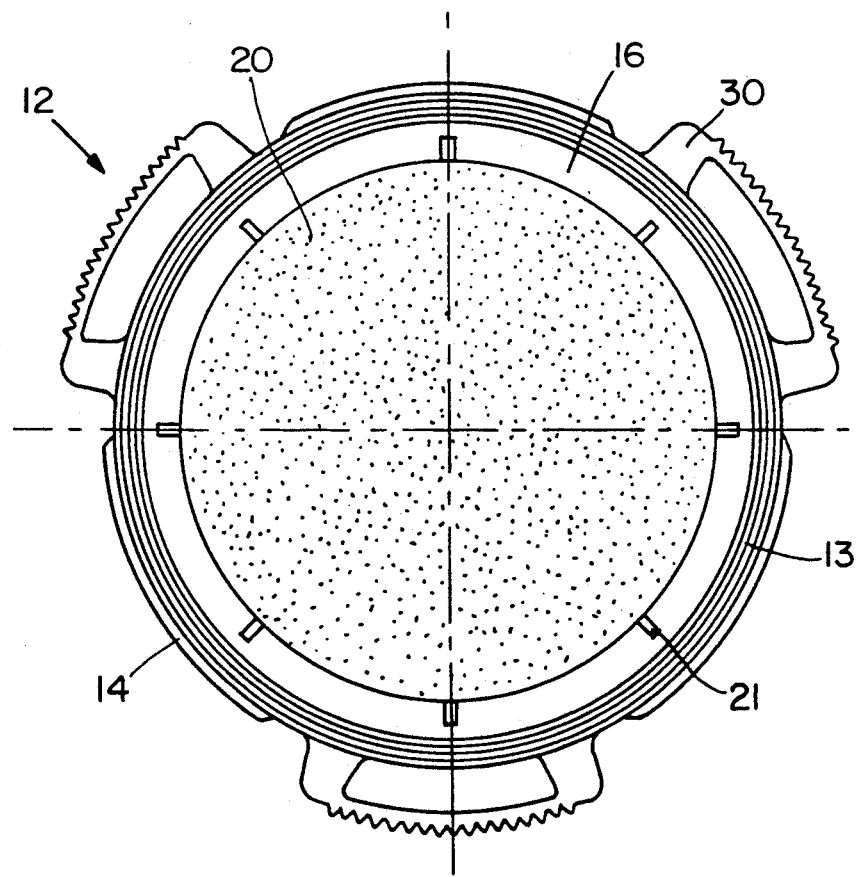
FIG. 4 is a plan view of the filtration support shown in FIG. 3.

The filtration support 12, which completes the device according to the invention, is shown in FIGS. 3 and 4 and comprises a chamber 13, which is generally cylindrical, fitted externally with a male threaded part 14 which may consist for example of three male threads, cooperating with the female threaded part 8 of the flange 7 of the container 1. If necessary, gripping components 30 may also be included.

The chamber 13 is closed at its upper part by a plate 15, comprising a circular peripheral ledge 16 and a network of circular 17 and axial 18 drainage channels terminating in an axial outlet orifice 19. The peripheral ledge 16 is axially prolonged slightly beyond the upper face of the plate 15 as shown in FIG. 3 in order to form a central circular cavity which serves to receive a disc-shaped removable porous aseptic insert 20 which rests on the top of the drainage channels.

The upper face of the insert 20, designed to enter into contact with the entire lower filtering surface of the membrane filter 4 to thereby support it when the support 12 is screwed into the container 1, lies at the same level as the upper face of the peripheral ledge 16. This ledge has a number of fine radial slits 21 to facilitate the subsequent removal of any liquid that has infiltrated between the downstream periphery of the membrane and the surface 16 through the porous aseptic insert 20.

Figure 7:
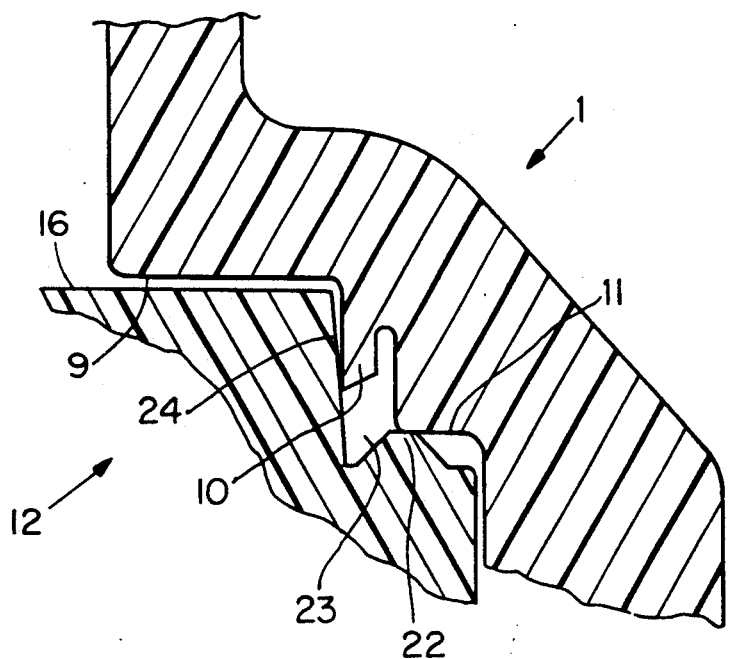
FIG. 7 is a cross-section of a first embodiment of the lip seal of the device according to the invention.

The connecting part between the threaded chamber 13 and the plate 15 of the filtration support 12 comprises, in the embodiment shown in FIG. 1, and as shown more clearly in FIG. 7, an outer shoulder 22, a circular gutter 23 and a sealing cone 24 delimiting the peripheral ledge 16. When the filtration support 12 is screwed inside the flange of the container 1, the shoulder 22 enters into contact with the stop 11 to prevent the crushing of the circular membrane (not shown in FIG. 7), and the sealing cone 24 deforms the inner face of the lip seal 10 to guarantee perfect tightness between the support 12 and the container 1.

Figure 8:
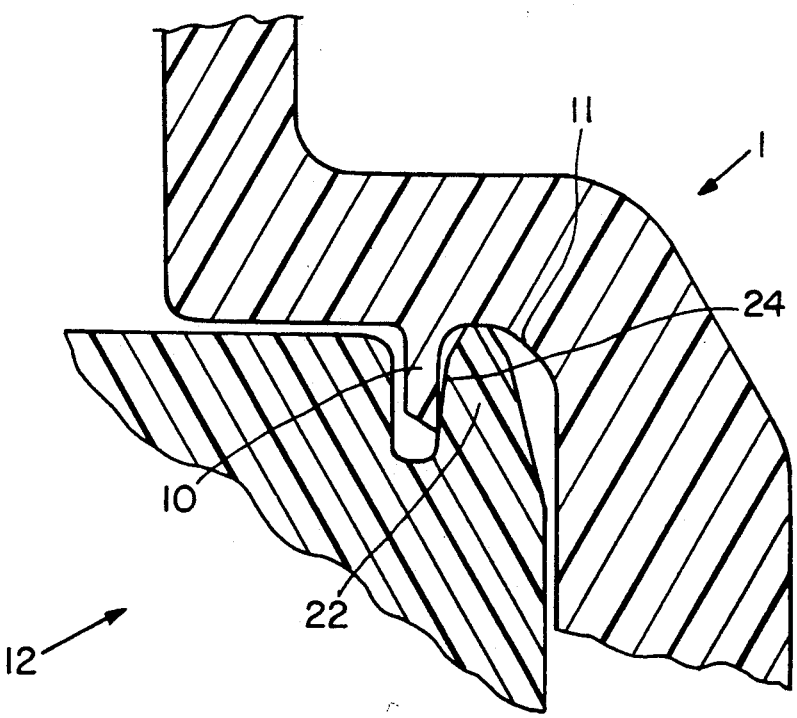
FIG. 8 is a cross-section of a second embodiment of the lip seal of the device according to the invention.

In another embodiment shown in FIG. 8, the outer shoulder 22 of the filtration support 12 not only enters into contact with the stop 11 of the container 1, but also includes a sealing cone 24 which deforms the outer face, and not the inner face, of the lip seal 10 thereby guaranteeing perfect tightness during the screwing of the support 12 into the container 1. The embodiment shown in FIG. 8 serves to carry out samplings of liquids to be analyzed at pressures higher than those that can be used with the embodiment in FIG. 7, i.e., as high as $6 \cdot 10^5$ Pa. This is due to the fact that any increase in the pressure of the liquid to be filtered tends to increase the tightness of the container against the sealing cone 24 of the filtration support 12.

The filtration support 12 may, for example, be made of a styrene polymer such as acrylonitrile/butadiene/styrene resin, and the insert 20 may, for example, be of sintered polyethylene. The incubation cartridge 25 designed to complete the device according to the invention may be a plastic cartridge for liquid (see FIG. 5) or dry culture medium (see FIG. 6).

This cartridge 25 comprises a chamber 26, which is generally cylindrical, containing a culture medium 27 appropriate to the microorganism to be detected, and which is externally fitted with a male threaded part 28 which can cooperate with the female threaded part 8 of the flange 7 of the container. This can consist, for example, of three male thread initiations for one, and corresponding female threads for the other, to guarantee rapid locking. The chamber 26 may also be provided with gripping components 29 and, at its top, a shoulder 37 designed to enter into contact with the stop 11 during the screwing of the cartridge 25 into the container 1.

Figure 5:
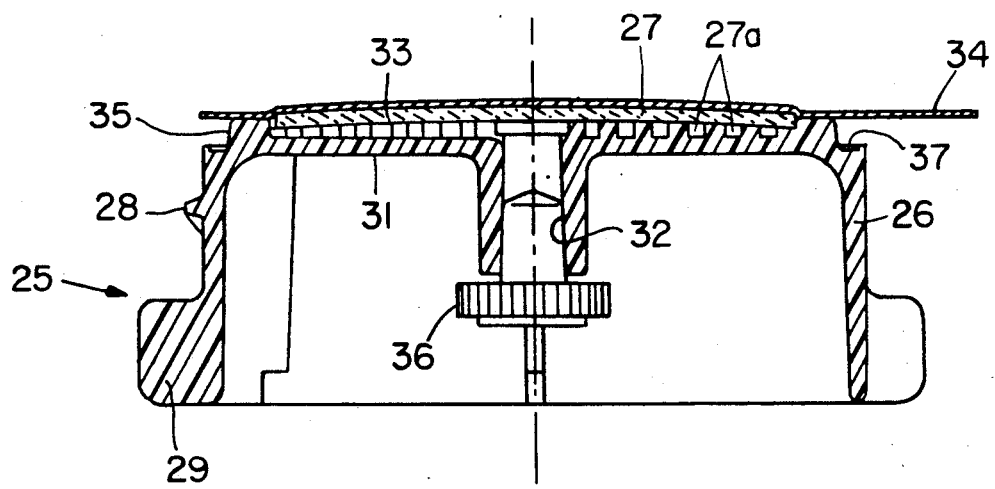
FIG. 5 is an elevation section of an incubation cartridge for liquid culture medium designed to cooperate with the container shown in FIGS. 1 and 2.

In the cartridge adapted for liquid culture medium shown in FIG. 5, the chamber 26 has, at its upper part, a support 31 that is externally convex and made of one piece with the chamber 26. This convex support 31 is fitted with a system of feed channels 27a connected to an axial feed orifice 32 closed by a removable plug 36. In addition, the convex support 31 is slightly recessed with respect to its peripheral ledge to form a central circular cavity, where an absorbent pad 33 impregnated with appropriate liquid culture medium rests. The pad can also be protected by a strippable protective paper 34 glued to the peripheral ledge.

The convex support 31 is connected to the upper end of the chamber 26 by a conical part 35 designed to cooperate with the lip seal 10 of the container 1 to prevent drying of the periphery of the liquid culture medium of the cartridge, which is screwed into the reservoir, during incubation.

Figure 6:
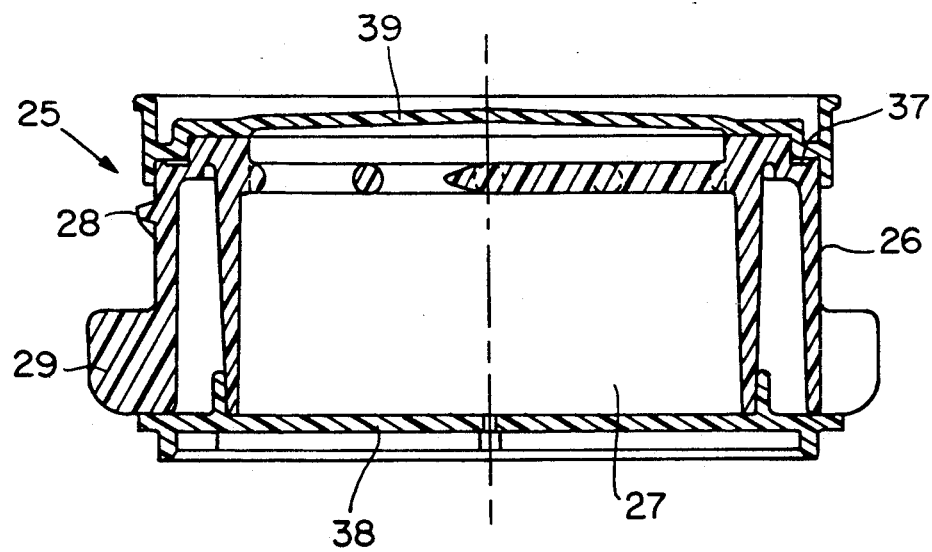
FIG. 6 is an elevation section of another incubation cartridge for dry culture medium designed to cooperate with the container shown in FIGS. 1 and 2.

The incubation cartridge for dry culture medium, shown in FIG. 6, does not have a conical sealing part, but its chamber 26 is closed at each end by a pair or removable lids 38 and 39. The lid 38, located opposite the shoulder 37, serves to fill the cartridge, and the lid 39, which is outwardly convex, is removed during the screwing of the cartridge 25 into the container 1. The plastic used to make the cartridge body may be polystyrene and that for the lids may be polypropylene.

The process according to the invention consists, after filling the cartridges with the suitable culture medium, of the operations required for microbiological testing directly at the location of the liquid sample to be tested. The process begins by screwing the one-piece container 1 to the filtration support 12 up to the sealing stop. The container forms a closed chamber that can withstand a filtration pressure of the liquid to be analyzed that is higher than $3 \cdot 10^5$ Pa in the embodiment shown in FIGS. 1, 3 and 7, and up to $6 \cdot 10^5$ Pa in the embodiment shown in FIG. 8.

Figure 9:
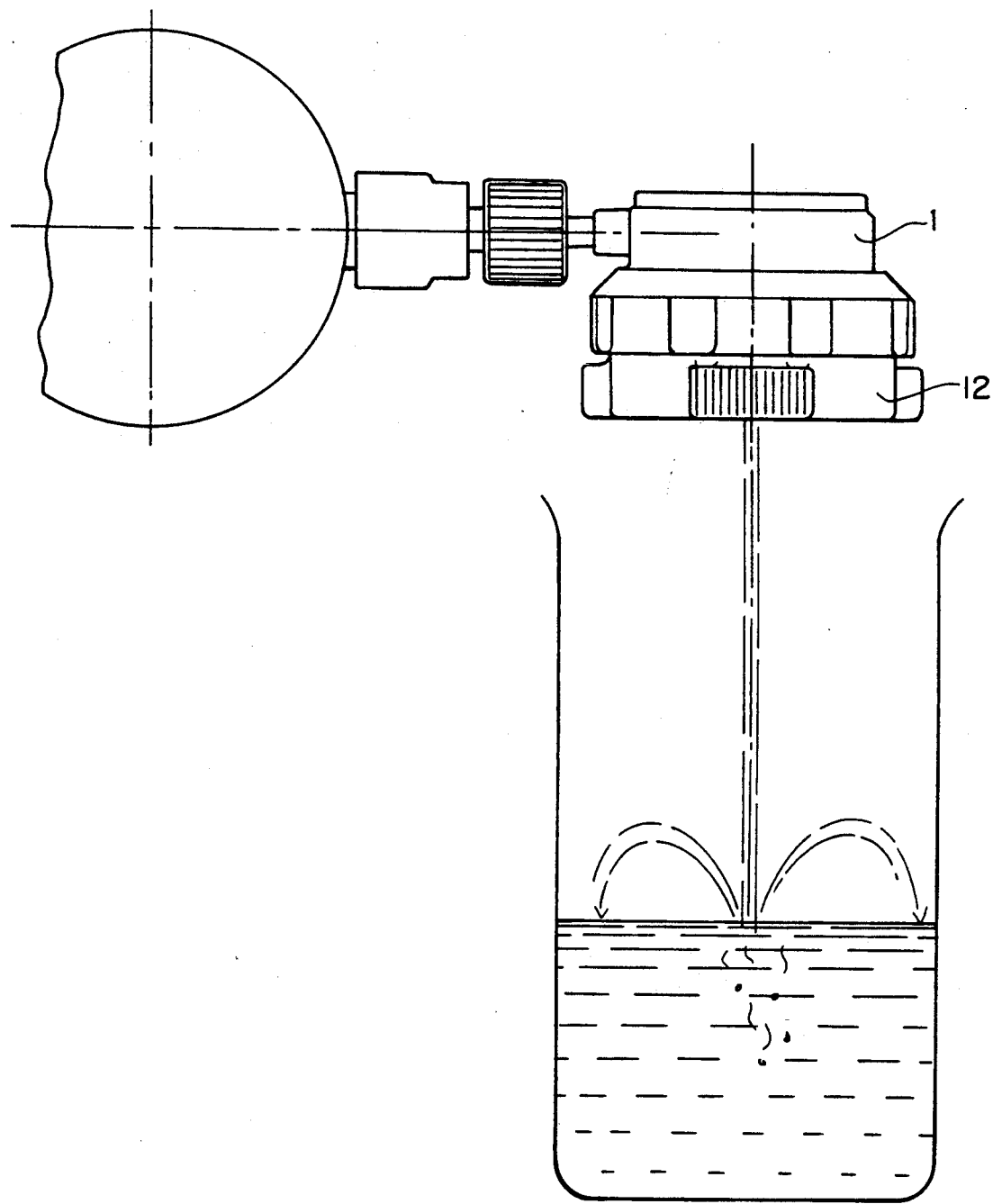
FIG. 9 is a view of a liquid sample to be tested with the device according to the invention during filtration.

The small male Luer plug 6 is then removed and the container 1 connected to the sample tap. The valve of the sample tap is opened, and the desired volume of liquid to be tested is allowed to filter through, and the sample volume is collected in a beaker located downstream from the filtration support (see FIG. 9). The sample tap valve is closed at the end of sampling, and the filtration unit is removed.

Figure 10:
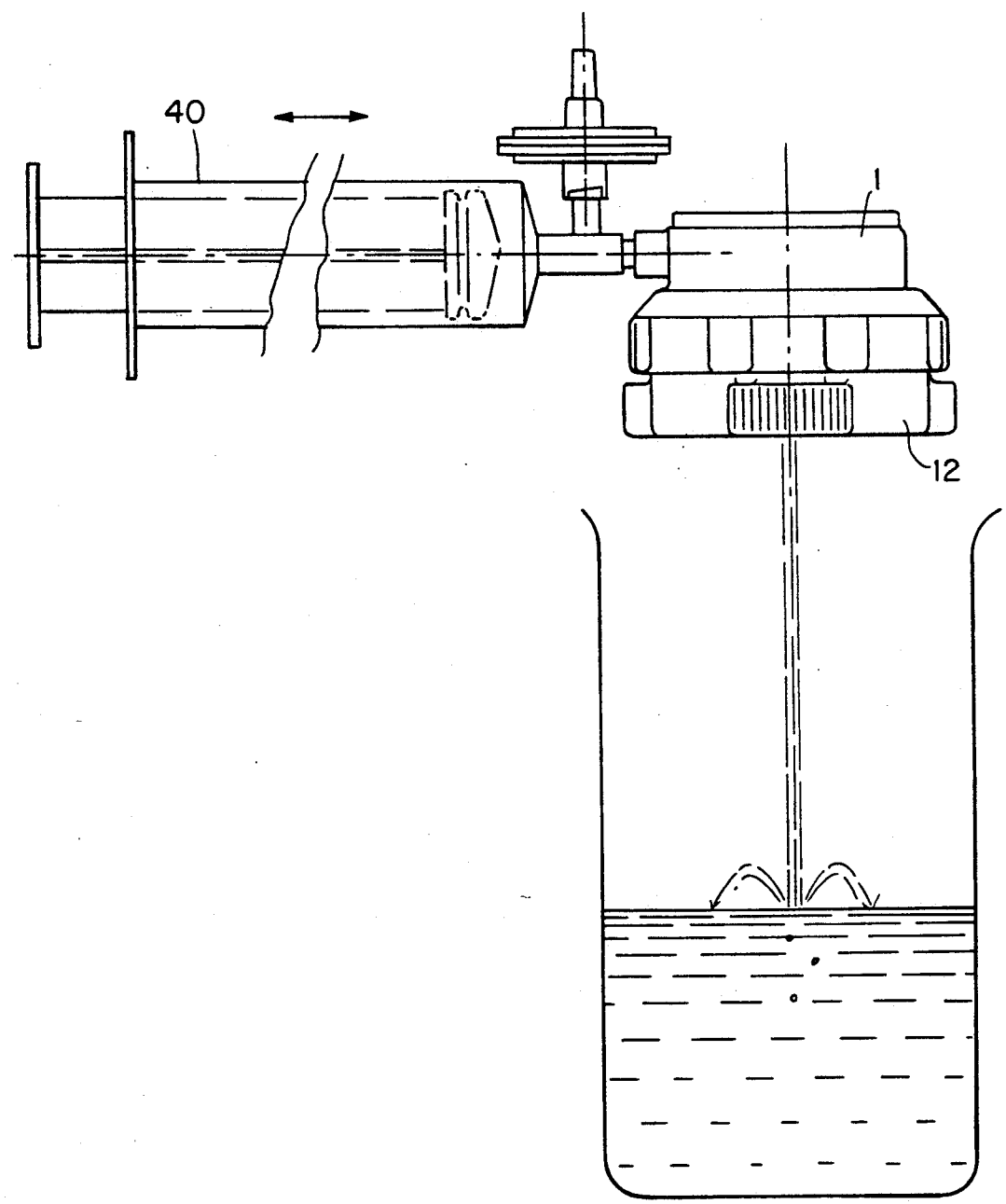
FIG. 10 is a view showing the termination of filtration of a sample by aseptic pressurization of the device according to the invention using a syringe.
Figure 11:
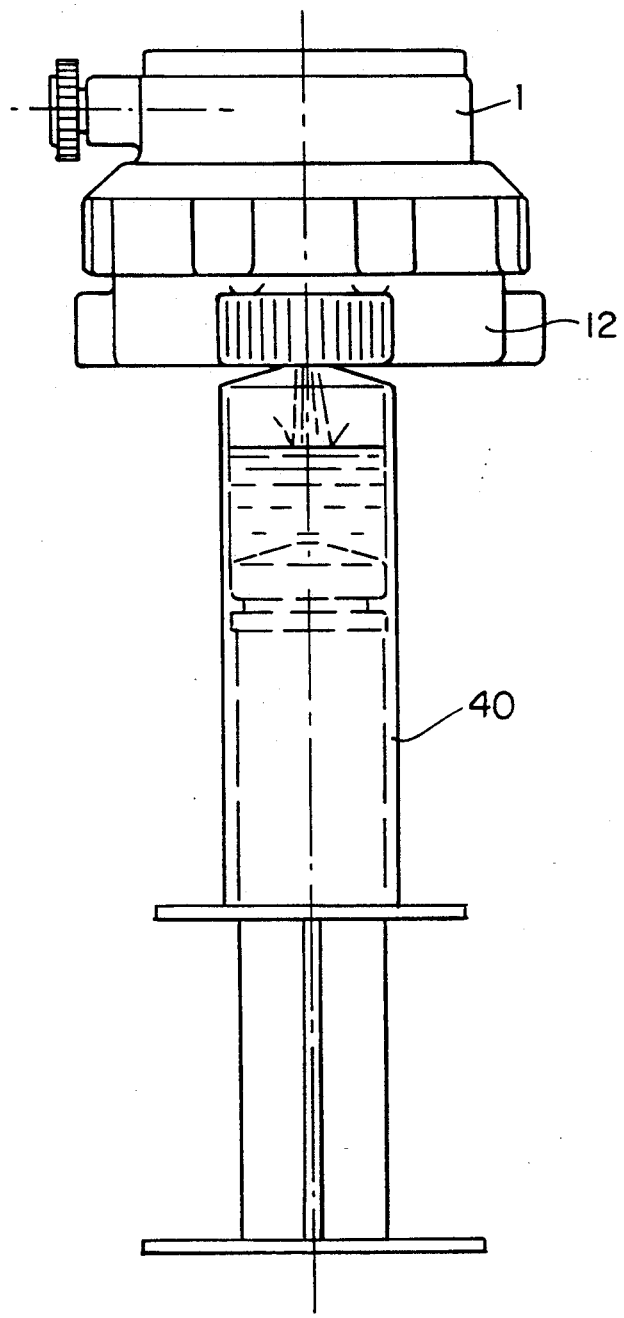
FIG. 11 is a view showing the termination of filtration of a sample by pumping of the remnant of the liquid using a syringe.

Filtration may be terminated by aseptically pressurizing the container by means of a syringe 40 fitted with an air filter, as shown in FIG. 10. This arrangement has the advantage of expelling all the liquid present upstream, downstream and in the pores of the membrane, thereby avoiding any risk of dilution of the culture medium downstream from the membrane filter. Alternatively, filtration may be terminated by causing a negative pressure to prevail by pumping the remnant of liquid with the aid of syringe 40 as shown in FIG. 11.

Figure 12:
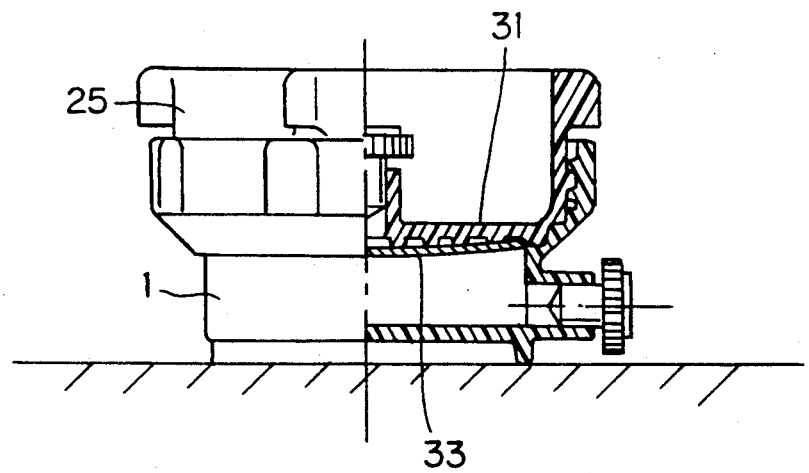
FIGS. 12 and 13 are views, partially in section, of the device according to the invention in reverse position in an incubator, and comprising an incubation cartridge for liquid or dry culture medium respectively.
Figure 13:
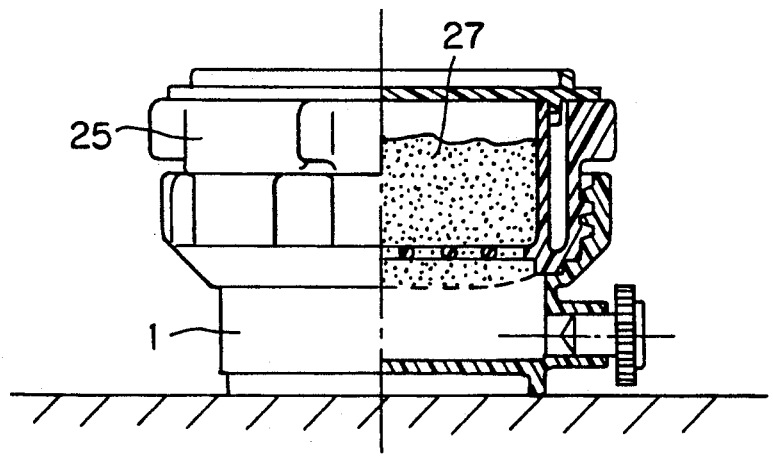

After the sample has been collected, the filtration support 12 is unscrewed and one of the cartridges 25 containing the desired culture medium is screwed in its place. Thereafter the overall unit consisting of the container 1 and the cartridge 25 is placed in reverse position in an incubator at the temperature and time duration required for the development of the colonies resulting from any microorganisms collected on the membrane filter 4, as shown in FIGS. 12 and 13.

It should be noted that the device according to the present invention also serves to collect a sample of product to be analyzed by means of a vacuum source connected to the filtration support 12, such as a vacuum syringe or flask. Such an alternative has heretofore been unavailable with previously known devices.

Figure 14:
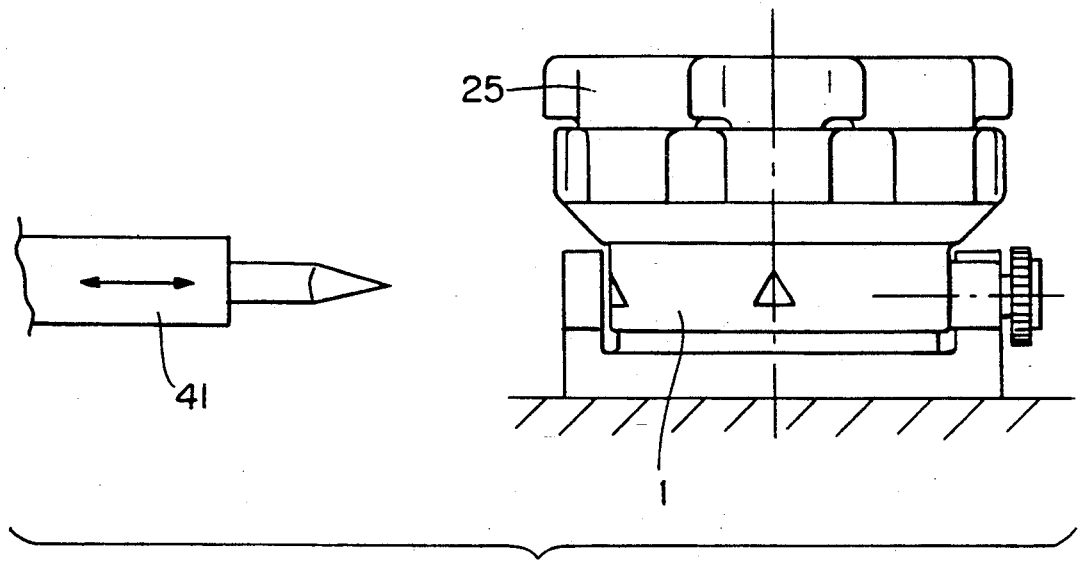
FIGS. 14 and 15 are views showing how the container of the device according to the invention can be perforated to reach the colonies for sampling and identification.
Figure 15:
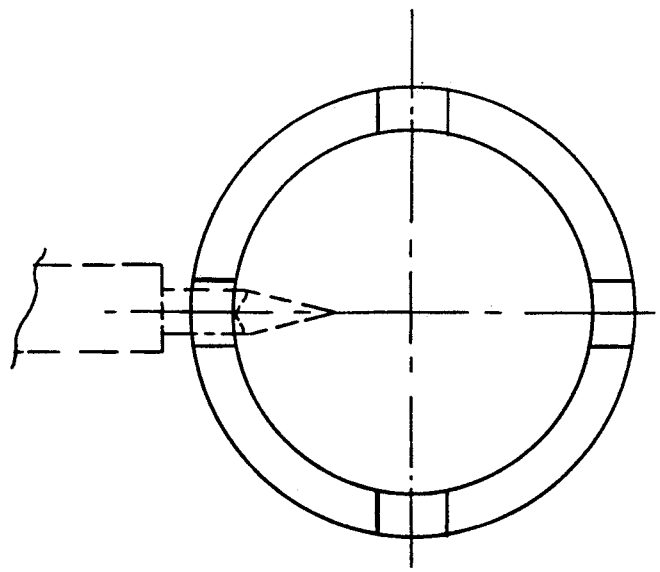

After development of the colonies, they can either be counted in place, as done in a Petri dish, since the reading window 3 is perfectly clear, or one or more of them can be identified by sampling, by perforating the container by means of an apparatus 41 designed for the purpose in order to be able to sample the desired colony with a platinum loop 42. With the container placed in a support, a cutting point with a triangular section penetrates the walls of the cylindrical body 2 of the container 1 parallel to the membrane filter, thus creating a completely clean hole without removal of any plastic (see FIGS. 14 and 15).

Figure 16:
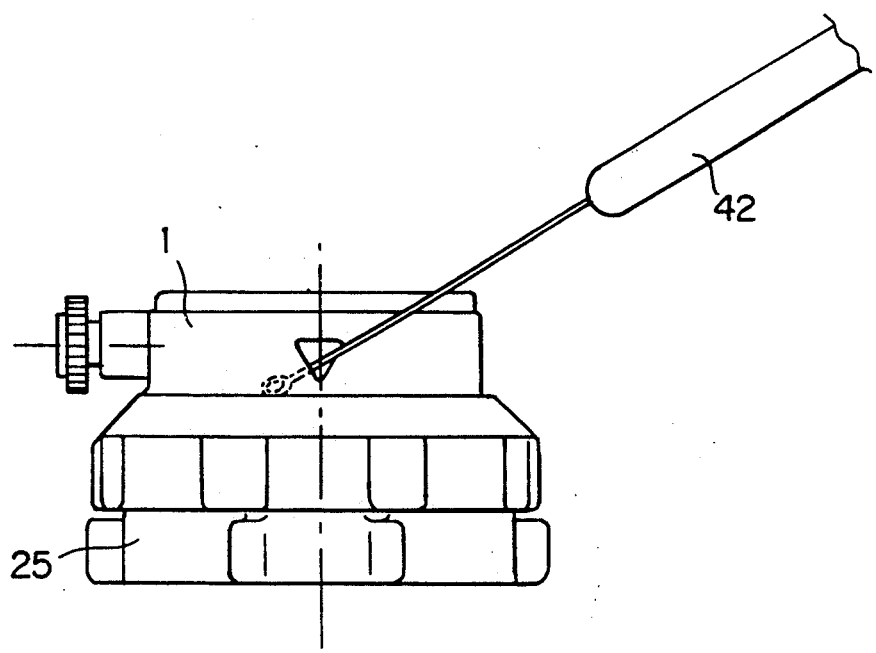
FIG. 16 is a view showing the sampling of a colony on the membrane of the device according to the invention.
Figure 17:
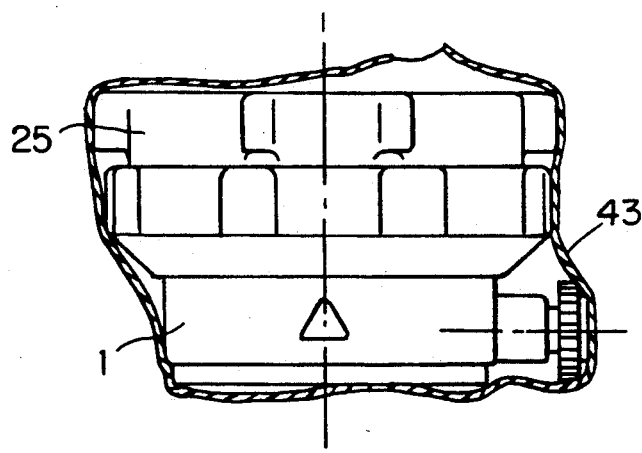
FIG. 17 is a view showing how the incubation of the device according to the invention can be continued after the sampling of a colony.

If so desired, it is possible to make several holes to make the colonies located on the surface of the filter membrane more accessible. In this case, it suffices to introduce the platinum loop 42 through the best-positioned hole to make the sampling (see FIG. 16). If it is desired to continue incubation, it suffices to envelop the test unit consisting of the container and the incubation cartridge in a suitable film 43 in order to isolate the container from the outside air (see FIG. 17).

I claim:

1. A device for the microbiological testing of a pressurized liquid sample comprising a completely closed container formed of a transparent plastic, a membrane filter, having an upstream surface and downstream surface pre-sterilized and for single use only, being sealed at the base of said completely closed container, said completely closed container having a liquid inlet adjacent the upstream surface of the membrane filter in the form of an orifice with an axis parallel to the plane of the membrane filter and which can be closed by a removable plug, said completely closed container being fitted, adjacent said upstream surface of the membrane filter with a built-in reading window and; adjacent said downstream surface of the membrane filter with a flange comprising a lip seal and a female threaded part.

2. The device according to claim 1 further comprising the completely closed container having a locking stop located between the lip seal and the female threaded part.

3. The device according to any one of claims 1 or 2 further comprising, the lip seal consisting of a circular tab having an inside face that tightly cooperates with a conical part of a removable element that can be screwed into the female threaded part of the completely closed container.

4. The device according to any one of claims 1 or 2 further comprising the lip seal consisting of a circular tab having an outer face that tightly cooperates with a conical part of a removable element that can be screwed into the female threaded part of the completely closed container.

5. The device according to claim 1, further comprising the built-in reading window which constitutes an upper face being located in a plane parallel to that of the membrane filter, and is cleared of any obstruction to avoid masking the view of the membrane filter, said built-in reading window capable of being perforated, by penetration, thereby making accessible the top of the membrane filter for any sampling of microbe colonies by means of a platinum loop.

6. The device according to any one of claims 1, 2, 3, 4 or 5, further comprising the transparent plastic of the completely closed container being formed of a copolymer of methyl methacrylate, butadiene and styrene.

7. The device according to claim 1, further comprising a filtration support made of plastic comprising a chamber fitted externally with a male threaded part cooperating with the female threaded part of the completely closed container, and an upper plate fitted with a system of drainage channels, terminating in an axial outlet orifice, said filtration support also comprising a sealing cone cooperating with the lip seal of the completely closed container to prevent any infiltration or contamination from the outside on the periphery of the filtration support during the filtration of a liquid sample to be analyzed.

8. The device according to claim 7, characterized in that a peripheral ledge of the upper plate of the filtration support is axially extended beyond the upper face of the upper plate to form a central circular cavity serving for the insertion of a removable porous aseptic insert, resting on the top of the system of drainage channels, and designed to enter into contact with the entire filtering surface of the membrane filter of the completely closed container.

9. The device according to claim 8, further comprising the filtration support being formed of a styrene polymer.

10. The device according to any one of claims 1, 5 or 6, further comprising an incubation cartridge made of plastic comprising a chamber containing a suitable culture medium for microorganisms and fitted externally with a male threaded part cooperating with the female threaded part of the completely closed container.

11. The device according claim 10, further comprising the incubation cartridge having a support convexed outward receiving an absorbent pad impregnated with liquid culture medium, which can be protected by a strippable protective paper, and in that an upper end of the chamber of the incubation cartridge displays a conical part designed to cooperate with the lip seal of the completely closed container to tightly fit on the downstream surface periphery of the membrane filter and thus to prevent any dehydration of the liquid culture medium during incubation.

12. The device according to any one of claims 10 or 11, further comprising the incubation cartridge formed of polystyrene.

* * * * *